United States Patent [19]

Haber et al.

[11] 4,401,107
[45] Aug. 30, 1983

[54] INTESTINAL CONTROL VALVE

[76] Inventors: Terry M. Haber, 25011 Castlewood, Lake Forest, Calif. 92630; William H. Smedley, 25371 Pacifica, Mission Viejo, Calif. 92691

[21] Appl. No.: 370,099

[22] Filed: Apr. 20, 1982

[51] Int. Cl.³ ............................................ A61F 1/00
[52] U.S. Cl. ........................... 128/1 R; 128/DIG. 25; 3/1
[58] Field of Search .......... 128/1 R, DIG. 25, 303 R; 3/1

[56] References Cited

U.S. PATENT DOCUMENTS 3,705,580  12/1972  Gauthier ...................... 128/DIG. 25
4,217,899   8/1980  Freier ........................... 128/DIG. 25

Primary Examiner—Dalton L. Truluck
Attorney, Agent, or Firm—Ralph B. Pastoriza

[57] ABSTRACT

The control valve is arranged to surround the anal-terminating descending intestine of a patient for realizing continence; that is function as an artificial sphincter. The valve itself comprises a stationary ring and a lower rotatable ring in an axially aligned position. A plurality of rods extends from the lower rotatable ring through aligned openings in the upper stationary ring. When the lower rotatable ring is rotated through an angle, the rods twist and their center portions radially contract inwardly in such a manner as to reduce the cross sectional area of the passage through the rings. By lining the rings and rods with a toroidal member, having an inner flexible part, rotation of the rotatable ring by an appropriate reversible drive motor will gently close off or open up the descending intestine portion of the patient.

9 Claims, 8 Drawing Figures

INTESTINAL CONTROL VALVE

FIELD OF THE INVENTION

The present invention relates to an intestinal control valve for surrounding the anal-terminating descending intestine of a patient, for realizing continence.

BACKGROUND OF THE INVENTION

Conventional colostomies involve a surgical procedure in which the intestine is severed and an end of the intestine is brought out through an incision in the abdominal wall of a patient. The securement of the intestine to the skin of the abdominal wall is such as to provide a passage for fecal matter outside the patient's body. The end opening of this passage is called the "stoma".

The foregoing type of operation results in a loss of continence for the patient and he or she must typically wear a pouch on the outside of the body in order to collect the fecal matter passing through the stoma. In order to avoid such incontinence, several types of closure devices have been proposed for closing off the stoma in order that a patient need not be burdened with the pouch.

Most such closure devices require a complicate surgical procedure, involving an invasion into the intestine itself. Further, any such closure device located on the abdominal wall or immediately beneath the abdominal wall in the area of the stoma is "unnatural" in its specific location.

BRIEF DESCRIPTION OF THE PRESENT INVENTION

With the foregoing in mind, the present invention contemplates the provision of a greatly improved closure device in the form of an intestinal control valve which can be surgically implanted without invading the intestine itself and furthermore which can be located at the anal end of the intestine in the normal or "natural" position of the sphincter muscle. Further, the design of this valve is such that it will close off the descending intestine of a patient in a manner analogous to the operation of the normal sphincter muscle, so that maximum comfort to the patient is realizable.

Briefly, the valve structure comprises an upper stationary ring and a lower rotatable ring in an axially aligned position with the stationary ring. A plurality of rods extend from the lower rotatable ring through aligned openings in the upper stationary ring in directions parallel to and spaced a given radial distance from the axis of the rings when the rotatable ring is in a first position. A toroidal member has an inner flexible part extending between the rings surrounding the anal-terminating descending intestine of a patient with the rods passing externally of the flexible part and an outer rigid part passing externally around the rings and rods. When the rotatable ring is now rotated within the toroidal member through a given angle to a second position, the rods are caused to twist and thereby decrease the given radial distance of the centers of the rods from the axis of the rings to thereby radially contract the flexible part to controllably reduce the passage through the anal-terminating descending intestine of the patient.

BRIEF DESCRIPTION OF THE DRAWINGS

A better understanding of this invention will be had by now referring to a preferred embodiment thereof as illustrated in the accompanying drawings in which.

DETAILED DESCRIPTION OF THE PREFERRED EMBODIMENT

Figure 1:
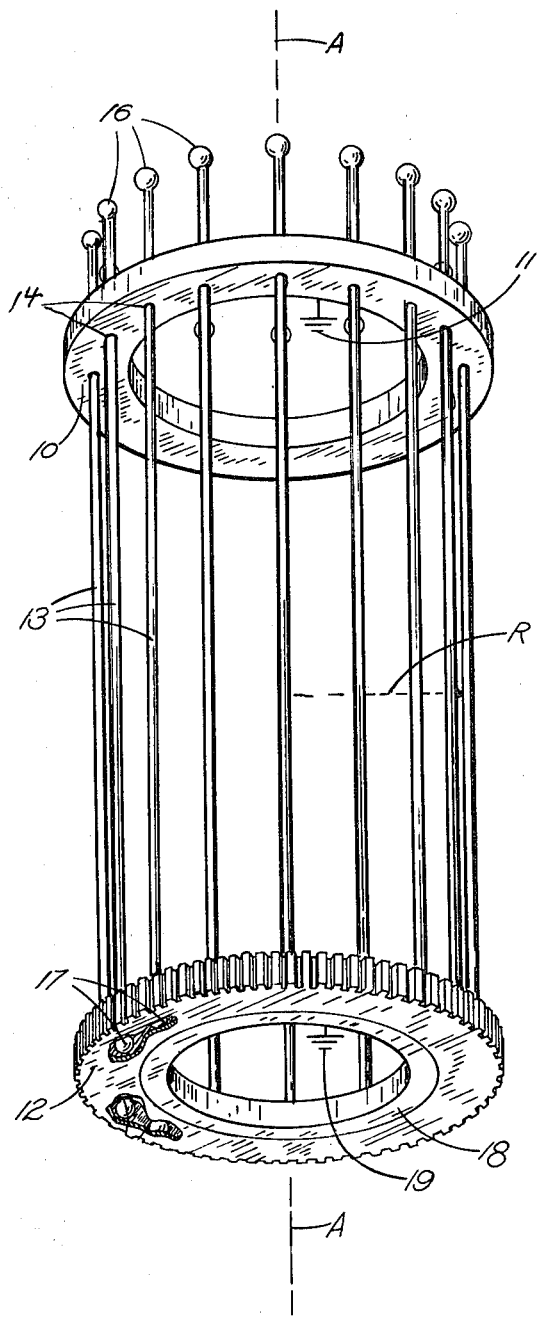
FIG. 1 is a schematic perspective view of some of the basic components of the control valve of this invention when the valve is in an open position.

Referring first to FIG. 1, there are illustrated certain basic components of the intestinal control valve. These components include an upper ring 10 to be held in a stationary position, as indicated by the dashed lines 11.

Cooperating with the upper ring 10 is a lower rotatable ring 12 and a plurality of rods 13 extending from the lower ring 12 through aligned openings 14 in the upper stationary ring. These rods pass in directions parallel to and spaced a given radial distance R from the axis A—A of the rings, when the rotatable ring 12 is in a first position as shown in FIG. 1.

The extending ends of the rods 13 from the upper ring 10 terminate in rounded spheres or small balls 16 so as to avoid any sharp edges. The lower ends of the rods are embedded in the lower ring in universal type ball and socket joints 17 so that the rods can twist or tilt with respect to the plane of the ring 12. A bearing 18 supports the ring 12 for rotation in its own plane, this bearing 18 in turn being held stationary as indicated by the small lines 19.

Figure 2:
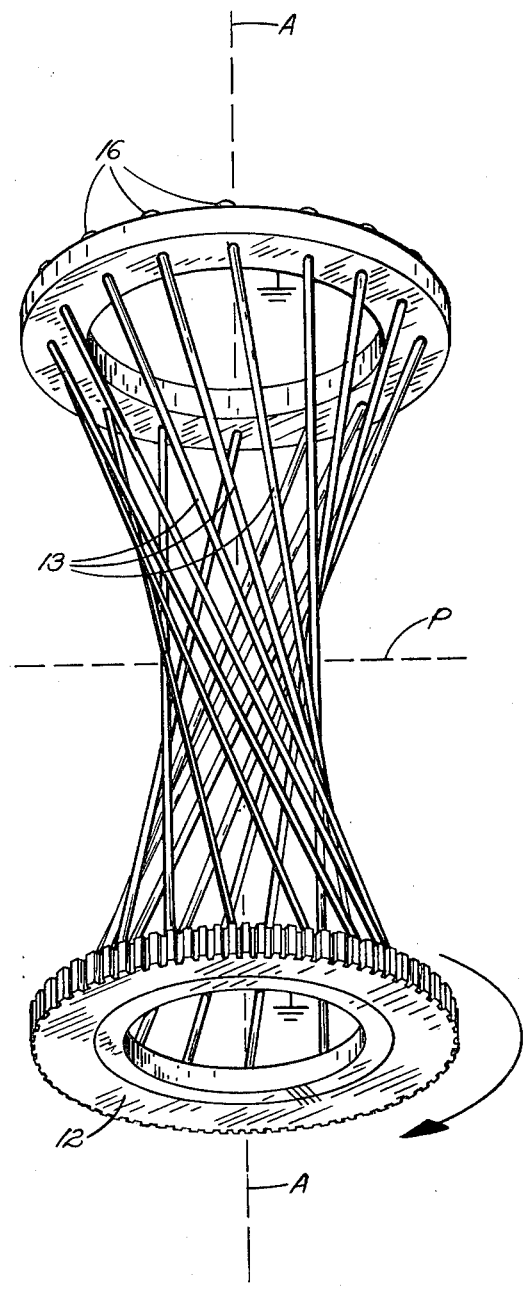
FIG. 2 is a view similar to FIG. 1, but illustrating the valve components in a "closed" position.

Referring to FIG. 2, the effect of rotating the rotatable ring 12 through a given angle indicated by the curved arrow is shown. Essentially, this action twists the rods 13 and retracts them through the openings in the upper ring, the balls 16 preventing complete withdrawal of the rods. As a consequence, the given radial distance R described in FIG. 1 is decreased, the centers of the rods from the axis of the rings moving radially inwardly at P to reduce the passage area through the device; that is, from the upper ring to the lower ring.

When the rotatable ring 12 is returned to its original position; that is, rotated back through the same given angle, then the rods will expand outwardly to the position illustrated in FIG. 1 to provide a maximum passage through the rings.

Figure 3:
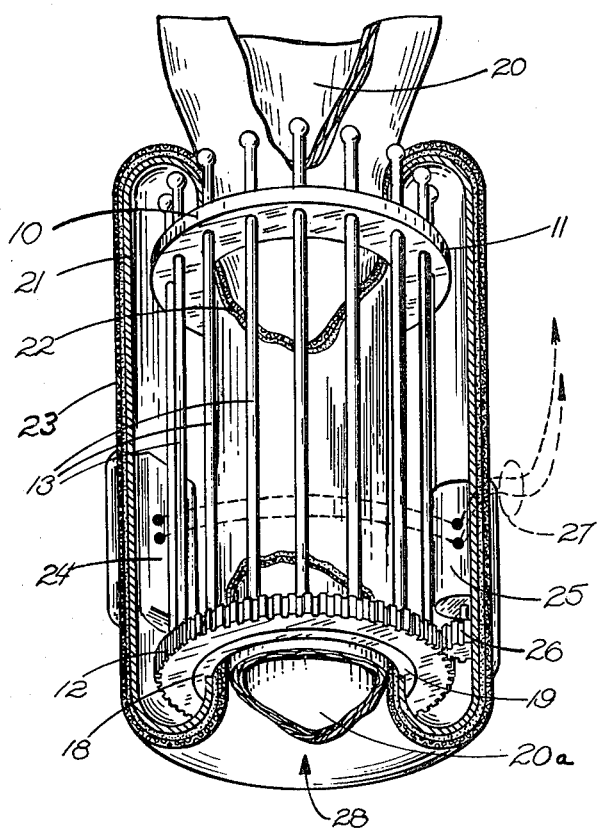
FIG. 3 is a cut-away perspective view of the valve components of FIG. 1 with additional components completing the entire valve structure, the same being shown surrounding the anal-terminating descending intestine of a patient.
Figures 4, 5:
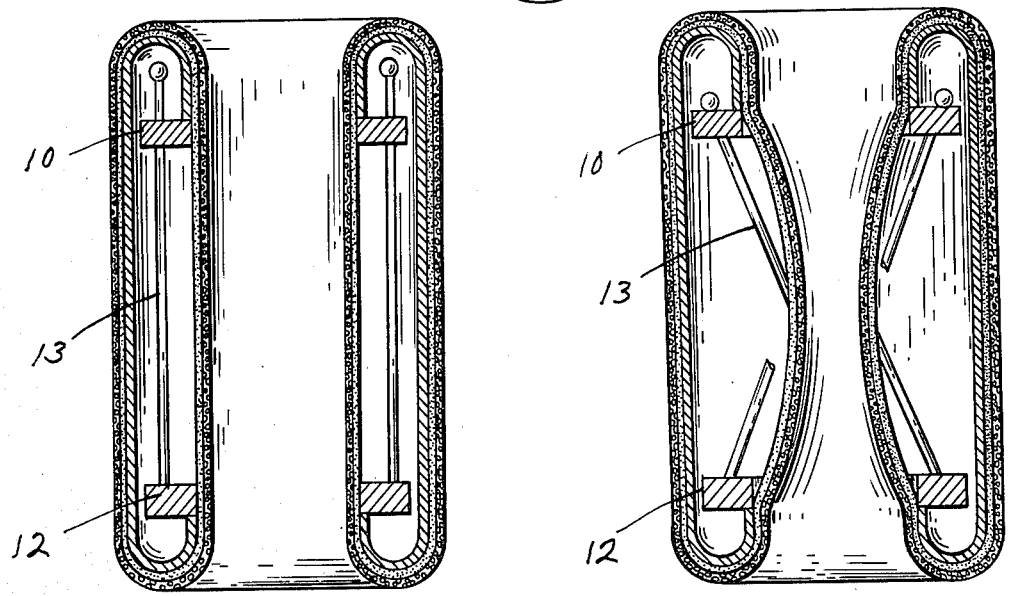
FIG. 4 is a cross-section of the valve in an open position.
FIG. 5 is another cross section similar to FIG. 4 but showing the valve in closed position.

Referring now to FIGS. 3, 4 and 5, the completed valve is illustrated surrounding the anal-terminating descending intestine of a patient for realizing continence. The upper part of this intestine comprises a collecting pouch as shown at 20, the descending intestine itself being indicated at 20a. A generally toroidally shaped member surrounds the skeletal framework of the valve described in FIGS. 1 and 2. More particularly, this toroidal member includes a rigid outer shell 21 constituting an outer part of the toroid passing externally around the rings and rods. The inner part of the toroid is made up of an inner flexible part 22 which might comprise a Dacron fabric interface with a flexible silicon-like covering 23 surrounding the entire shell and flexible part of the toroidal member. It will be noted that the rings and rods are wholly encased or incorporated within the toroidal member.

Supported within the rigid shell 21 is a battery pack 24 for energizing an appropriate drive motor 25 also secured within the shell 21. Drive motor 25 has a drive pinion gear 26 in meshing engagement with the lower rotatable ring 12 as shown best in FIG. 3. Appropriate switch means to be described connect to the motor as indicated by the dashed lines 27, the switch means being located exterior of the toroidal member.

Referring to FIG. 4, the valve is shown in open position to provide for a maximum passage through the lower intestine out the lower opening.

FIG. 5 is the same as FIG. 4, but shows the valve in closed position wherein the twisted rods will gently and controllably reduce the passage through the anal-terminating descending intestine 20a shown in FIG. 3.

Figure 6:
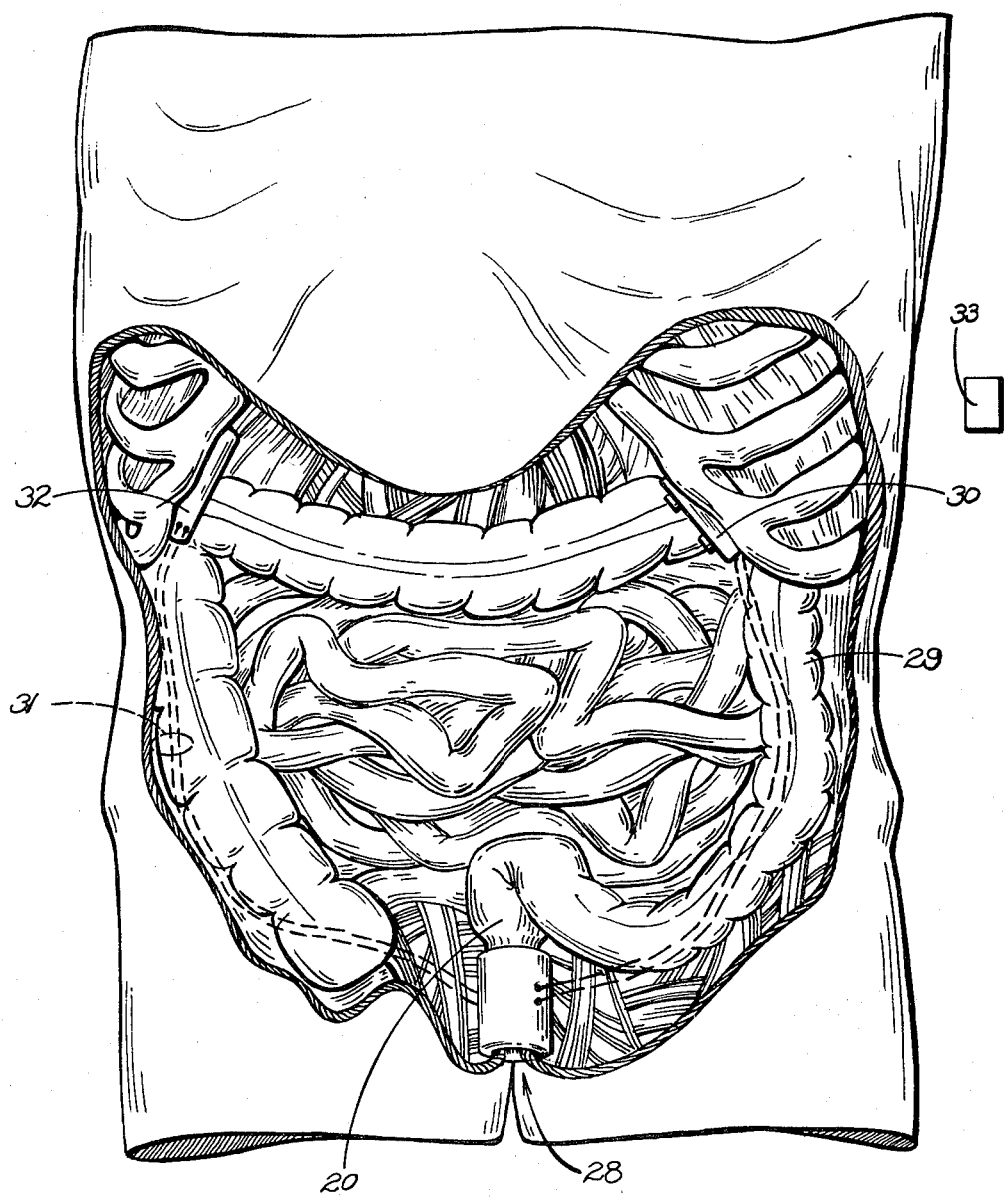
FIG. 6 is a cut-away view of a patient's body showing the manner in which the valve is incorporated therein along with operating components therefor.

Referring now to FIG. 6, the control valve described in FIGS. 3 to 5 is shown at the lower end of the patient's large intestine, the lower end of the valve coinciding in position to the anal opening 28. The main portion of the large intestine itself is shown at 29 and the switch means for connecting power to the drive motor described in FIG. 3 is indicated at 30 under the left lower rib of the patient. It should be understood, however, that this switch means may be implanted subcutaneously exterior of the toroidal member at any convenient surgically accessible location in the patient's body.

In FIG. 3, the battery pack 24 was described as being incorporated in the toroidal member. However, it is possible and in certain cases preferable to have the battery pack separate from the toroidal member or exterior thereof for convenient replacement or recharging. Thus, in the embodiment of FIG. 6, there are shown electrical connections 31 in the form of dotted lines passing from the motor in the valve to battery pack 32 disposed under the patient's right rib. Again, however, as in the case of the switch means, the battery pack 32 may be implanted subcutaneously at any convenient surgically accessible location in the patient's body.

In a preferred embodiment, the battery pack 32 is of the rechargeable type by means of induction so that the pack can be recharged from the exterior of the patent's body without having to invade the skin.

The switch means 30 as described in FIG. 6 may incorporate a logic circuit and timer for periodically operating the drive motor in forward and reverse directions to close and open the valve at predetermined time intervals and for predetermined periods of time. In this respect, an automatic operation of the valve can be realized for the patient's optimum comfort in a manner similar to that of a pacemaker, pacing a person's heart.

In accord with further features of this invention, it is possible to incorporate a receiver means responsive to transmitted signals within the switch means 30 to close and open the valve. In such event, a remote transmitter means such as indicated at 33 in FIG. 6 wholly exterior of the body would be used for generating such signals.

Figure 7:
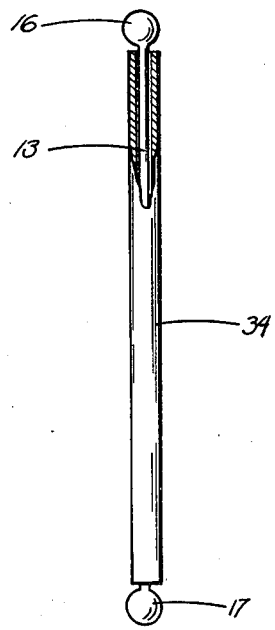
FIG. 7 is a schematic showing of one of the valve components illustrating an additional optional feature; and, FIG. 8 is a cross-section showing a cooperating suppository utilized with the control valve.

Referring now to FIG. 7, there is shown a rotatable flurocarbon polymer friction-reducing sleeve 34 surrounding the rod making up one of the plurality of rods 13 described in FIGS. 1 and 2. This showing is provided simply to indicate that such a friction-reducing sleeve could be provided on all of the rods 13 described in FIGS. 1 and 2, these sleeves engaging the flexible part of the toroidal member to provide for complete freedom of movement of this flexible part.

Figure 8:
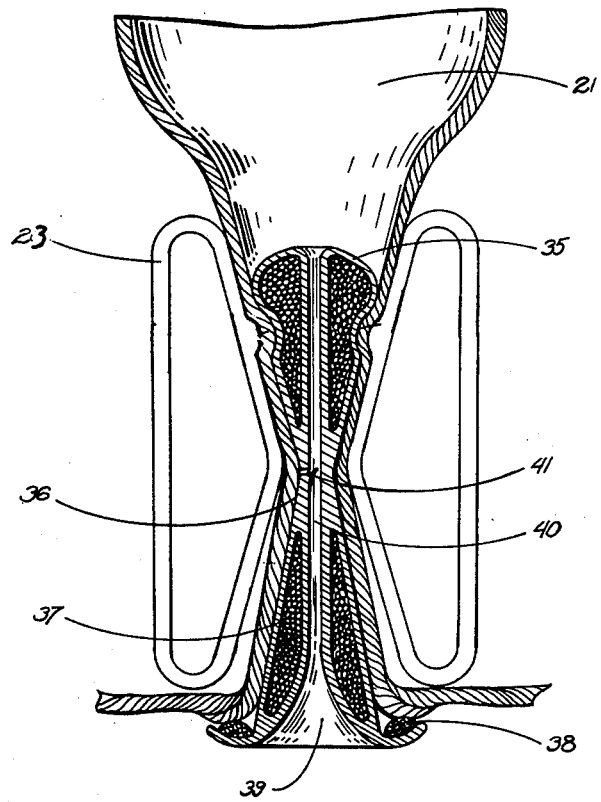

Referring now to FIG. 8, there is shown at 35 a cooperating suppository of generally tubular shape. This suppository has a flexible outer skin 36 covering a spongy interior 37. The tubular shape terminates at its lower end in an annular pad 38 preferably incoporating anti-bacterial medicine. The lower outlet end of the suppository is indicated at 39 and constitutes the terminating end of an internal passage 40, serving as an enema and gas venting channel.

The suppository is receivable in the anal-terminating end of the descending intestine to aid in uniform intestinal compression by the valve and cushion delicate exposed intestinal mucosa.

From all of the foregoing, it will now be appreciated that the present invention has provided a greatly improved intestinal control valve wherein a primary feature is the fact that it is non-invasive of the intestine itself; that is, the valve is designed to exert a gentle squeezing action as a consequence of the twisting rods, all as described. There is no need to pierce or puncture the intestine in any manner.

The cooperating suppository as described in FIG. 8 would, of course, be changed as required. The thickness of the suppository walls and the provision of upper and lower bulges as illustrated assure the suppository will remain in proper position within the lower intestine and within the valve body itself. The "tightness" of the closed position of the valve can, of course, be controlled by the "thickness" of the walls of the cooperating suppository. A gas escape port and flap 41 may be added.

Various changes falling within the scope and spirit of this invention will occur to those skilled in the art. The intestinal control valve accordingly is not to be thought of a limited to the exact embodiment set forth merely for illustrative purposes.

We claim:

1. An intestinal control valve for surrounding the anal-terminating descending intestine of a patient for realizing continence, said valve including in combination:
 (a) an upper stationary ring;
 (b) a lower rotatable ring in an axially aligned position with said stationary ring;
 (c) a plurality of rods extending from said lower rotatable ring through aligned openings in said upper stationary ring in directions parallel to and spaced a given radial distance from the axis of the rings when the rotatable ring is in a first position; and
 (d) a toroidal member having an inner flexible part extending between the rings surrounding the anal-terminating descending intestine with the rods passing externally of the flexible part and an outer rigid part passing externally around the rings and rods whereby rotation of said rotatable ring within said toroidal member through a given angle to a second position twists the rods to decrease the given radial distance of the centers of the rods from the axis of the rings to thereby radially contract said flexible part to controllably reduce the passage through the anal-terminating descending intestine.

2. A valve according to claim 1, including a drive gear to drive said lower rotatable ring; a drive motor secured to said rigid part of said toroidal member for driving said gear; a battery pack for supplying electrical energy to said drive motor; and switch means for connecting said battery pack to said motor for driving said motor in first and second directions to close and open said valve.

3. A valve according to claim 2, in which said battery pack is secured within said toroidal member.

4. A valve according to claim 2, in which said battery pack is implanted subcutaneously exteriorally of said toroidal member at a convenient surgically accessible location in the patient's body and wherein said switch means is also implanted subcutaneously exteriorally of the toroidal member at a convenient, surgically accessible location in the patient's body.

5. A valve according to claim 2, in which said switch means incorporates a logic circuit and timer for periodically operating said motor in forward and reverse directions to close and open said valve at predetermined time intervals and for predetermined periods.

6. A valve according to claim 2, in which said switch means includes receiver means responsive to transmitted signals to close and open said valve; and a remote transmitter means exterior of the patent's body for generating said signals.

7. A valve according to claim 1, in which each of said rods is surrounded by a rotatable fluorocarbon polymer friction reducing sleeve engaging said flexible part of said toroidal member to provide for complete freedom of movement of said flexible part.

8. A valve according to claim 4, in which said battery pack is of the rechargeable type by means of induction so that the battery pack can be recharged from the exterior of the patient's body without invading the skin.

9. A valve according to claim 1, including a cooperating suppository of tubular shape having a flexible outer skin covering a spongy interior and terminating at its lower end in an annular pad impregnated with anti-bacterial medicine, the inner passage of said tubular shape serving as an enema and gas vent channel, said supository being receivable at the anal-terminating end of the descending intestine to aid in uniform intestinal compression by said valve and to cushion delicate exposed intestinal mucosa.

* * * * *

Notice of Adverse Decision in Interference

In Interference No. 101,254, involving Patent No. 4,401,107, T. Haber and W. Smedley, INTESTINAL CONTROL VALVE, final judgment adverse to patentees was rendered Feb. 20, 1985, as to claim 1.

[*Official Gazette April 30, 1985.*]